US009506605B2

(12) United States Patent
Paget et al.

(10) Patent No.: US 9,506,605 B2
(45) Date of Patent: Nov. 29, 2016

(54) PROCESS FOR PRODUCING BIOMETHANE FOR INJECTION INTO A GAS NETWORK FROM A PLURALITY OF PRODUCTION SITES AND SET OF DEVICES FOR THE IMPLEMENTATION THEREOF

(71) Applicant: L'Air Liquide, Societe Anonyme pour l'Etude et l'Exploitation des Procedes Georges Claude, Paris (FR)

(72) Inventors: Nicolas Paget, Grenoble (FR); Pierre Roux, St. Etienne de Crossey (FR)

(73) Assignee: L'Air Liquide Société Anonyme Pour L'Étude Et L'Exploitation Des Procedes Georges Claude, Paris (FR)

( * ) Notice: Subject to any disclaimer, the term of this patent is extended or adjusted under 35 U.S.C. 154(b) by 54 days.

(21) Appl. No.: 14/514,803

(22) Filed: Oct. 15, 2014

(65) Prior Publication Data

US 2015/0101671 A1    Apr. 16, 2015

(30) Foreign Application Priority Data

Oct. 15, 2013 (FR) ..................... 13 60013

(51) Int. Cl.
*F17D 1/04* (2006.01)
*B01D 53/14* (2006.01)
(Continued)

(52) U.S. Cl.
CPC ................ *F17D 1/04* (2013.01); *B01D 53/14* (2013.01); *B01D 53/1475* (2013.01); *B01D 53/22* (2013.01); *C12M 21/04* (2013.01); *C12M 23/36* (2013.01); *C12M 23/58* (2013.01); *C12M 41/40* (2013.01); *C12M 47/18* (2013.01);
(Continued)

(58) Field of Classification Search
CPC .. B01D 53/14; B01D 53/1475; B01D 53/22; B01D 2257/504; B01D 2258/05; C12M 21/04; C12M 23/36; C12M 23/58; C12M 41/40; C12M 47/18; F17D 1/04
See application file for complete search history.

(56) References Cited

U.S. PATENT DOCUMENTS 6,955,704 B1 * 10/2005 Strahan .................. B01D 53/22
                                                              95/14
7,497,894 B2 * 3/2009 Jeffers ................... B01D 53/22
                                                              95/52

(Continued)

FOREIGN PATENT DOCUMENTS

DE    20 2011 004 421    6/2011
FR         2 983 848    6/2013

OTHER PUBLICATIONS

Search Report and Written Opinion for FR1360013, mailed Jul. 1, 2014.

*Primary Examiner* — Jason M Greene
(74) *Attorney, Agent, or Firm* — Christopher J. Cronin

(57) ABSTRACT

The present invention relates to the production of biomethane intended for supplying a natural gas network from n biogas production plants Ii, with i varying from 1 to n, in which each of the plants produces and stores the biogas which is collected at each of the plants via a mobile collection device and the collected biogas is purified so as to produce biomethane which is subsequently injected into a natural gas network. The invention also makes provision for storing the biogas, partially purified biogas, or biomethane in order to ensure the continuity of the supply of biomethane to the network during the collection round.

17 Claims, 1 Drawing Sheet

(51) Int. Cl.
　　*B01D 53/22* (2006.01)
　　*C12M 1/107* (2006.01)
　　*C12M 1/00* (2006.01)
　　*C12M 1/34* (2006.01)

(52) U.S. Cl.
　　CPC ....... *Y02E 50/343* (2013.01); *Y10T 137/0318* (2015.04); *Y10T 137/86035* (2015.04)

(56) References Cited

U.S. PATENT DOCUMENTS

| | | | |
|---|---|---|---|
| 8,007,567 B2 | 8/2011 | Roe et al. | |
| 2003/0225169 A1* | 12/2003 | Yetman | C01B 3/34 518/726 |
| 2005/0061001 A1 | 3/2005 | Maston | |
| 2006/0213370 A1* | 9/2006 | Leonard | B01D 53/14 96/243 |
| 2008/0134754 A1* | 6/2008 | Funk | B01D 53/1475 73/23.41 |
| 2009/0314625 A1* | 12/2009 | Renaud | C12M 21/04 203/38 |
| 2010/0037772 A1* | 2/2010 | Roe | B01D 53/1425 96/6 |
| 2010/0051546 A1* | 3/2010 | Vuong | B01D 61/027 210/637 |
| 2010/0119890 A1* | 5/2010 | Frisbie | H01M 8/0662 429/408 |
| 2013/0095014 A1* | 4/2013 | Grill | C12M 47/18 423/219 |
| 2013/0224819 A1 | 8/2013 | Rivard | |
| 2014/0004599 A1* | 1/2014 | Boote | C12M 21/04 435/290.1 |
| 2014/0246358 A1* | 9/2014 | Gravett | B03C 3/017 209/17 |

* cited by examiner

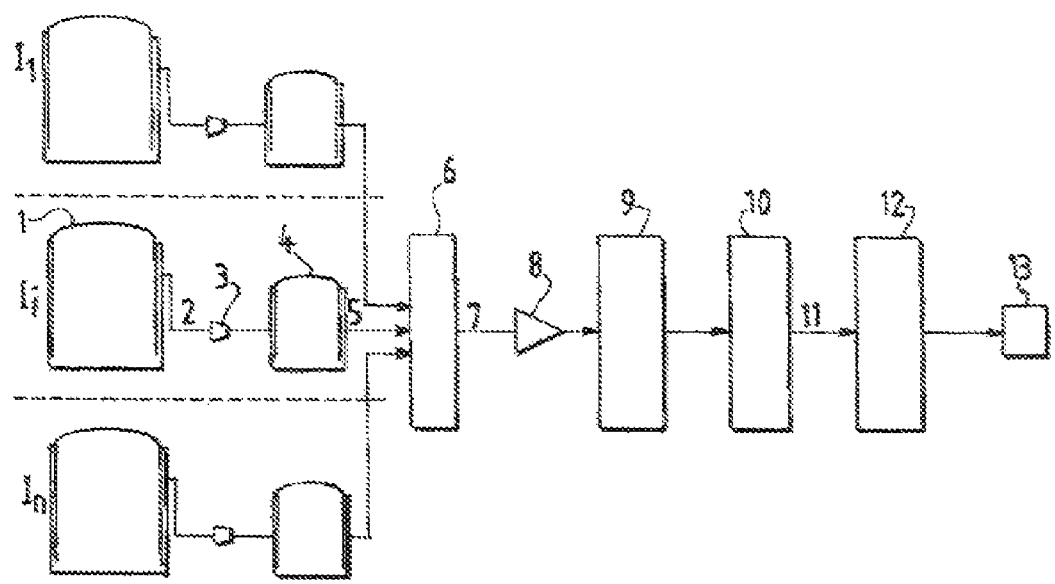

PROCESS FOR PRODUCING BIOMETHANE FOR INJECTION INTO A GAS NETWORK FROM A PLURALITY OF PRODUCTION SITES AND SET OF DEVICES FOR THE IMPLEMENTATION THEREOF

CROSS-REFERENCE TO RELATED APPLICATIONS

This application claims the benefit of priority under 35 U.S.C. §119 (a) and (b) to French patent application No. 1360013, filed Oct. 15, 2013, the entire contents of which are incorporated herein by reference.

BACKGROUND

Field of the Invention

The present invention relates to a process for producing biomethane intended for supplying a natural gas network from a plurality of biogas production plants, comprising the steps of producing, storing, purifying to biomethane and supplying the network, and also to a set of devices for the implementation of the process.

Related Art

Within the context of the upgrading thereof, biomethane—as a renewable substitute for natural gas that has the same properties as the latter—may be injected into a natural gas distribution or transport network that makes it possible to connect gas producers and consumers.

A natural gas distribution or transport network makes it possible to supply consumers with natural gas. The network is maintained at a pressure between 2 and 6 bar for distribution, 15 and 25 bar for medium-pressure distribution and 25 and 80 bar for transport.

Biogas is a gas produced by the natural or controlled fermentation of plant or animal organic matter (methanization). It predominantly contains methane ($CH_4$) and carbon dioxide ($CO_2$), but also, in smaller proportions, water, nitrogen, hydrogen sulphide, oxygen, and also other organic compounds, in trace amounts.

Depending on the organic matter and the techniques used, the proportions of the components differ, but on average biogas comprises, as dry gas, from 30% to 75% methane, from 15% to 60% $CO_2$, from 0 to 15% nitrogen, from 0 to 5% oxygen and trace compounds.

Added more recently to the upgrading—mainly on-site or nearby—of biogas is that of biogas purified to the specifications of natural gas. Biomethane may be used as a non-fossil substitute for natural gas thus supplementing natural gas resources with a renewable portion produced at the heart of territories. It can be used for exactly the same uses.

The methods of upgrading biomethane are determined as a function of local contexts: local energy requirements, possibilities of upgrading as biomethane fuel, existence nearby of networks for distributing or transporting natural gas in particular. Creating synergies between the various operators working in a territory (farmers, manufacturers, public authorities), the production of biomethane helps territories to acquire greater energy self-sufficiency.

In order to produce and use biomethane as renewable natural gas in natural gas networks, two main players are involved: the first of these players is the biomethane producer, the second player is the natural gas distributor who manages the gas network.

In order to have the option of injecting biomethane into an existing gas network, it is necessary to provide the plant with a metering station (for example GRdF or GRT Gaz [French gas distribution network companies] injection posts) and to provide the connection to the nearby network. The pressure of the gas in the network may vary and will sometimes require an additional compression in order to permit the injection.

Therefore, when a biogas producer wishes to use his gas to produce biomethane for injecting into a network, he has to face, in all cases, the installation and maintenance costs of the injection system; also sometimes, in certain cases, additional constraints are imposed on the biogas producer:
  technical constraints of the network operator which require sizeable investments, and/or
  minimum volume of biogas to be produced which often exceeds the production capacity of small producers (agricultural producers, private producers or others).

To date, no solution exists for these small biogas producers which enables them to produce biogas intended for injection into a natural gas network.

There is therefore a need for a solution for producing biomethane—available for being injected into a network—that makes it possible to treat a plurality of small-volume biogas productions with a view to producing biomethane for a limited cost for the producers.

There is also a need, for the natural gas network managers, to have sufficient and reliable supplies of biomethane with a view to increasing the portion of renewable gas in the gas circulating in the network.

There is therefore a need for a solution that provides the producers with the upgrading of their biogas productions that are too small to be upgraded individually and which provides supplies of biomethane for a natural gas distribution or transport network from a plurality of biogas productions.

SUMMARY OF THE INVENTION

According to the invention, a process is hence proposed for producing biomethane intended for supplying a natural gas network from n biogas production plants Ii, with i varying from 1 to n, comprising at least the following steps:
  for each of the biogas production plants Ii, a step $a_i$ of producing biogas Pi,
  for each of the biogas production plants Ii, a step $b_i$ of storing the biogas produced Pi,
  a step c of collecting all of the biogases Pi produced and stored at each of the plants Ii via a mobile collection device,
  a step d of purifying the biogas collected so as to produce biomethane,
  a step e of injecting the biomethane into the natural gas network.

The above process operates in the following manner: each of the biogas production plants Ii produces its biogas $P_i$ and stores it between two successive collections; the mobile collection device circulates between the production plants $I_i$. When the collection device arrives at the site of the plant $I_i$, it collects the gas present in the storage tank of the plant then returns to the plant $I_{i+1}$ to likewise collect therefrom the biogas produced and itself previously stored also. The biogas collected (sum of the biogases $P_i$) is treated in order to produce biomethane. The conversion is not carried out individually by each small producer, a purification device associated with the collection treats all of the biogas productions which considerably reduces the cost for the biogas producer. The network is then supplied from the biomethane resulting from all of the productions, it is more reliable, both in terms of quality and volume.

Depending on the case, the process of the invention may comprise all or some of the features herein below.

For at least some of the biogas production plants $I_i$, the biogas $P_i$ is subjected to a compression step before being stored at the site of the plant; the storage of the biogas at the site of the producer may indeed be a storage at the pressure of the methanizer of the production plant, but the producer may favour storage at a higher pressure in order to limit the volume stored before collection. The total biogas storage capacity at the site of the producer is adapted to the frequency at which the collection device passes through; the storage tank will in general allow two days of storage, however, its capacity could be limited if the collection rotation is short.

Depending on the requirements, the injection of biomethane into the network is continuous or in batch mode. In order for the injection into the network to be carried out continuously, it is necessary to make provision to store the gas under pressure after collection; for this purpose, one or more high-pressure buffer storage tanks are provided for storing the gas after collection.

In particular, this could be storage of the biogas collected, and/or storage of partially purified biogas, and/or storage of biomethane. Gas is preferably stored close to the injection station. Owing to this buffer storage tank, there will be no break in the supplying of the network during the collection. Thus, depending on the case, the process of the invention may comprise either a step of compressing the biogas followed by a step of storing the biogas under pressure prior to the purification step, or a step of compressing partially purified biogas followed by a step of storing the partially purified biogas under pressure when a first portion of the purification is carried out via a mobile purification device, or else a step of compressing the biomethane followed by a step of storing the biomethane under pressure when the purification step is carried out integrally via a mobile purification device.

According to a second aspect of the invention, the latter relates to a set of devices suitable for carrying out the process of the invention.

It thus relates to a set of devices intended to supply a natural gas network from n biogas production plants $I_i$, with i varying from 1 to n, comprising at least:

n plants $I_i$ capable of carrying out n productions $P_i$ of biogas, for each plant $I_i$, a means of storing the biogas produced, for at least some of the plants $I_i$, a means of compressing the biogas $P_i$ prior to the storage thereof, a mobile collection device capable of collecting all of the stored biogases $P_i$, a device for purifying the collected biogas so as to produce biomethane, a device for injecting the biomethane into the natural gas network to be supplied.

The mobile device for collecting biogas from the producers preferably contains a means of compression for filling an integrated mobile gas storage means. This mobile storage means is preferably a tank lorry or lorry equipped with racks of cylinders suitable for transporting pressurized gas, but other means of transport suitable for particular situations may be envisaged (river transport, rail transport or other). The transportation means will naturally have to comply with the regulations in force; for transporting gas by lorry for example, it will thus be necessary to refer to the road regulations in force.

The device for purifying the biogas in order to produce biomethane could comprise all or some of the modules below using conventional purification technologies; mention is made here, by way of example, of certain means and technologies that may be used:

a drying module using a technology from among the following: molecular sieve, chiller heat exchanger, membranes;

one or more module(s) for abating pollutants such as $H_2S$, COv, COvSi, $NH_3$, using activated charcoal, regenerative or non-regenerative washing with sodium hydroxide, membrane, washing with water, iron oxide, regenerable or non-regenerable sieve, biological washing, washing with amines, washing with liquid $CO_2$, etc.;

a $CH_4/CO_2$ separation module using selective membranes, washing with water, pressure swing adsorption (PSA), washing with amines, washing with liquid $CO_2$, cryogenic system, etc.;

modules for treating effluents and vents, using, for the treatment of the latter, thermal oxidizer, gas boiler, biological filter, etc.;

an optional compression module for storage.

According to one particular embodiment of the invention, all or part of the device for purifying the collected biogas may be mobile. The various treatment means or a part thereof may be mobile and placed on a means of transport shared between themselves and/or with gas storage means, or may be mobile and separate.

Alternatively, when the whole of the device for purifying the collected biogas is fixed, it is preferably set up close to the station for injecting biomethane into the network.

The plant may comprise one or more means of storing gas after collection.

In particular, when all or part of the purification device is mobile, the gas stored could be partially purified biogas, but will be in general biomethane under pressure, the storage means being installed close to the injection station. Alternatively, when the purification device is fixed, the storage could be a storage of biogas.

The device for injecting the biomethane into the gas network must comprise analysis and metering means, necessary for validating the quality and the invoicing; it is located at an injection station defined by the operator of the network (guaranteeing the quality and metering of the biomethane transferred to the network).

BRIEF DESCRIPTION OF THE FIGURES

The FIGURE illustrates block diagram illustrating various components of the invention starting from n production sites referenced Ii.

DETAILED DESCRIPTION OF THE INVENTION

The invention will now be better understood by means of the following description given with reference to the appended FIGURE.

The FIGURE presents a block diagram illustrating various components of the invention starting from n production sites referenced Ii.

For the sake of simplicity, the FIGURE reproduce, among the n production sites, only three sites identified as $I_1$, Ii and In. Still for the sake of simplicity, only the essential elements present of the plant $I_i$ are referenced. The operation of the invention is described by referring to this site $I_i$.

According to the diagram of the FIGURE, each production site $I_i$ comprises a methanizer 1, producing a biogas 2, the biogas is compressed in a compressor 3, then stored in a tank 4 for storing the biogas $P_i$ produced on the site, these various elements being connected to one another by pipes that transport the biogas produced. The biogas $P_i$ is compressed in order to occupy a smaller storage volume; however, compression of the biogas is not obligatory—it may also be imagined that certain production sites do not compress their biogas, whilst others do compress it. The biogas $P_i$ produced by each site Ii referenced 5 is collected by the collection means 6. According to the variant represented in the FIGURE, the biogas collected 7 is compressed by the compressor 8 and stored in a storage tank 9 before being purified via the purification device 10. The purification device 10 is located close to the site of injection into the network. The purification device is unique for the set of production plants. The biomethane produced 11 supplies the biomethane injection 13 and metering system 12 located at the injection station in order to be checked, metered and injected into the network.

The diagram does not reproduce all of the components of use for the production and treatment of the biogas and of the biomethane, but mainly the components of use for understanding the invention; thus the components contained in the purification device, and also in the injection station have not been indicated since the detail of these components is not necessary for describing the operation of the invention and these components are known to a person skilled in the art.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A process for supplying biomethane to a natural gas network from n biogas production plants, wherein n is greater than 1, comprising the steps of:
   producing biogas at each of the biogas production plants;
   storing each of the produced biogases at a respective one of the biogas production plants in a respective high-pressure buffer storage tank;
   collecting all of the stored biogases via a mobile collection device circulating between the biogas production plants;
   purifying the collected biogas to produce biomethane; and
   injecting the biomethane into the natural gas network,
   wherein the step of collecting all of the stored biogases via a mobile collection device is performed before the step of purifying the collected biogas.

2. The process of claim 1, further comprising the step of compressing the biogas produced at some or all of the biogas production plants before said step of storing.

3. The process of claim 1, further comprising the steps of:
   partially purifying collected biogas;
   compressing the partially purified biogas; and
   storing the compressed partially purified gas under pressure.

4. The process of claim of claim 3, wherein said step of partially purifying is carried out by a mobile purification device.

5. The process of claim 1, further comprising the step of storing the biomethane before said step of injecting.

6. The process of claim 1, wherein the mobile collection device is a lorry, a tank lorry, a river transport device, or a rail transport device.

7. The process of claim 6, wherein the mobile collection device is a lorry or tank lorry including a compressor and being equipped with racks of cylinders suitable for transporting pressurized biogas.

8. The process of claim 1, wherein said step of purifying is performed by:
   a drying module comprising one of a molecular sieve, a chiller heat exchanger, and membranes;
   one or more pollutant abatement modules for abating $H_2S$, COv, COvSi, or $NH_3$, said pollutant abatement modules using a technique selected from the group consisting of activated charcoal, regenerative washing with sodium hydroxide, non-regenerative washing with sodium hydroxide, membranes, washing with water, iron oxide, regenerable sieves, non-regenerable sieves, biological washing, washing with amines, and washing with liquid $CO_2$;
   a $CH_4/CO_2$ separation module using a technique selected from the group consisting of selective membranes, washing with water, pressure swing adsorption (PSA), washing with amines, washing with liquid $CO_2$, and cryogenics; and
   an effluent/vent treatment module using a technique selected from the group consisting of thermal oxidizers, gas boilers, and biological filters.

9. The process of claim 1, wherein said step of purifying is carried out by a mobile purification device.

10. The process of claim 1, wherein said step of purifying is carried out by a fixed purification device.

11. The process of claim 1, wherein said step of injecting is carried out by an injection device comprising an analysis and metering device for validating a quality of the biomethane and invoicing of the biomethane.

12. A system for supplying biomethane to a natural gas network from n biogas production plants, wherein n is greater than 1, said system comprising:
   n biogas production plants;
   one or more high-pressure buffer storage tanks disposed at each of said n biogas production plants;
   a mobile collection device adapted to circulate between the biogas production plants and collect biogas in said storage tanks;
   a biogas purification device adapted to purify biogas to produce biomethane after the mobile collection device circulates between the biogas production plants and collects the biogas in said storage tanks; and
   a biomethane injection station adapted to receive biomethane from said biogas purification device and inject the received biomethane into the natural gas network.

13. The system of claim 12, wherein the biogas purification device receives biogas from the mobile collection device and is fixed and disposed at the biomethane injection station.

14. The system of claim 12, further comprising a compressor disposed at least some of the biogas production plants adapted to compress the biogas so that it can be stored in the respective high pressure buffer storage tanks under pressure.

15. The system of claim 12, further comprising a mobile partial purification device adapted to partially purify biogas, wherein the biogas purification device receives partially purified biogas from the mobile partial purification device.

16. The system of claim 15, further comprising a compressor adapted to receive partially purified biogas from said mobile purification device and the biogas purification device receives partially purified biogas from the mobile partial purification device via the compressor.

17. The system of claim 12, further comprising:
   a compressor receiving biomethane from the biogas purification device and compressing the received biomethane; and
   a biomethane storage device receiving compressed biomethane from the compressor, wherein the biomethane injection station received biomethane from the biogas purification device via the compressor and biomethane storage device.

* * * * *